US009958372B2

(12) United States Patent
Matsuura

(10) Patent No.: US 9,958,372 B2
(45) Date of Patent: May 1, 2018

(54) PARTICLE DETECTION APPARATUS AND PARTICLE DETECTION METHOD

(71) Applicant: AZBIL CORPORATION, Chiyoda-ku (JP)

(72) Inventor: Yuho Matsuura, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 201 days.

(21) Appl. No.: 15/134,538

(22) Filed: Apr. 21, 2016

(65) Prior Publication Data
US 2016/0313250 A1    Oct. 27, 2016

(30) Foreign Application Priority Data

Apr. 23, 2015    (JP) .................................. 2015-088349

(51) Int. Cl.
*G01N 21/64*    (2006.01)
*G01N 15/02*    (2006.01)
(Continued)

(52) U.S. Cl.
CPC ..... *G01N 15/0211* (2013.01); *G01N 15/1459* (2013.01); *G01N 2015/0046* (2013.01);
(Continued)

(58) Field of Classification Search
CPC .............. G01N 21/27; G01N 21/6486; G01N 21/3577; G01N 15/0612; G01N 15/0211;
(Continued)

(56) References Cited

U.S. PATENT DOCUMENTS 3,733,547 A * 5/1973 Coulter .............. G01N 15/1227
324/71.1
5,225,886 A * 7/1993 Koizumi ................ G01N 21/94
356/237.4
(Continued)

FOREIGN PATENT DOCUMENTS

JP    6-52232     2/1994
JP    3049254     3/2000
(Continued)

OTHER PUBLICATIONS

Norio Hasegawa et al., "Instantaneous Bioaerosol Detection Technology and its Application," Yamatake Corporation, Azbil Technical Review, issued Dec. 2009, pp. 2-7, 2009).

*Primary Examiner* — David Porta
*Assistant Examiner* — Djura Malevic
(74) *Attorney, Agent, or Firm* — Oblon, McClelland, Maier & Neustadt, L.L.P.

(57) ABSTRACT

A particle detection apparatus includes a plurality of photodetectors that detect reaction light generated at a particle irradiated with inspection light and generate electric signals in respective channels; pulse detectors that detect pulses of the electric signals in the respective channels; a correlating unit that correlates the pulse of the electric signal in a reference channel being a channel having a highest signal-to-noise (S/N) ratio, with the pulse of the electric signal in a channel other than the reference channel generated within a predetermined time difference range with respect to the pulse of the electric signal in the reference channel; and an attribute specifying unit that specifies an attribute of the particle on the basis of the correlated pulses of the electric signals.

14 Claims, 6 Drawing Sheets

(51) Int. Cl.
*G01N 15/14* (2006.01)
*G01N 15/00* (2006.01)

(52) U.S. Cl.
CPC ............... *G01N 2015/1486* (2013.01); *G01N 2015/1493* (2013.01)

(58) Field of Classification Search
CPC ...... G01N 15/147; G01N 15/14; G01N 15/10; G01N 15/1488; G01N 15/1456
See application file for complete search history.

(56) References Cited

U.S. PATENT DOCUMENTS

| | | | | |
|---|---|---|---|---|
| 7,060,992 B1* | 6/2006 | Barney | ............... | G01N 15/1459 250/458.1 |
| 7,295,319 B2* | 11/2007 | Kajii | ............... | G01N 21/6402 356/433 |
| 7,430,046 B2* | 9/2008 | Jiang | ............... | G01N 15/0205 356/336 |
| 7,973,929 B2* | 7/2011 | Bates | ............... | G01N 15/1012 356/336 |
| 8,188,438 B2* | 5/2012 | Li | ............... | B01L 3/50273 250/364 |
| 8,218,144 B2* | 7/2012 | Jiang | ............... | G01N 15/0205 340/630 |
| 8,513,614 B2* | 8/2013 | Kraft | ............... | G01T 1/1647 250/370.09 |
| 8,717,550 B2* | 5/2014 | Janka | ............... | G01N 15/1459 356/335 |
| 9,057,703 B2* | 6/2015 | Suzuki | ............... | G01N 15/0612 |
| 9,109,987 B2* | 8/2015 | Kinugasa | ............... | G01N 15/0211 |
| 9,291,542 B2* | 3/2016 | Kinugasa | ............... | G01N 15/1434 |
| 9,297,740 B2* | 3/2016 | Murakami | ............... | G01N 15/1404 |
| 9,494,779 B2* | 11/2016 | Tanabe | ............... | G01N 21/6408 |
| 9,671,346 B2* | 6/2017 | Hosoi | ............... | G01N 21/6486 |
| 9,672,329 B2* | 6/2017 | Vickers | ............... | G06F 19/366 |
| 9,683,940 B2* | 6/2017 | Hosoi | ............... | G01J 1/42 |
| 9,835,552 B2* | 12/2017 | Wagner | ............... | G01N 21/3577 |
| 2004/0078500 A1* | 4/2004 | Pezzini | ............... | G06F 13/385 710/36 |
| 2004/0262501 A1* | 12/2004 | Kajii | ............... | G01N 21/6402 250/227.24 |
| 2006/0238757 A1* | 10/2006 | Silcott | ............... | G01N 15/0618 356/338 |
| 2007/0013910 A1* | 1/2007 | Jiang | ............... | G01N 15/0205 356/336 |
| 2011/0019186 A1* | 1/2011 | Himmelhaus | ............... | G01N 21/648 356/317 |
| 2011/0141454 A1* | 6/2011 | Henning | ............... | G01N 15/06 356/51 |
| 2011/0256551 A1* | 10/2011 | Linder | ............... | B01L 3/5027 435/7.1 |
| 2012/0147370 A1* | 6/2012 | Jiang | ............... | G01N 15/0205 356/338 |
| 2012/0154348 A1* | 6/2012 | Okuno | ............... | C12Q 1/06 345/204 |
| 2012/0274937 A1* | 11/2012 | Hays | ............... | G01S 17/58 356/337 |
| 2012/0310060 A1* | 12/2012 | Baker, Jr. | ............... | A61B 5/14551 600/324 |
| 2013/0077087 A1* | 3/2013 | Janka | ............... | G01N 15/1459 356/72 |
| 2014/0078500 A1* | 3/2014 | Jiang | ............... | G01N 15/0205 356/246 |
| 2014/0255980 A1* | 9/2014 | Hasegawa | ............... | C12Q 1/04 435/34 |
| 2014/0340681 A1* | 11/2014 | Murakami | ............... | G01N 15/1404 356/337 |
| 2015/0160112 A1* | 6/2015 | Kinugasa | ............... | G01N 15/0211 250/365 |
| 2015/0160131 A1* | 6/2015 | Kinugasa | ............... | G01N 21/64 250/252.1 |
| 2015/0160133 A1* | 6/2015 | Kinugasa | ............... | G01N 15/1434 250/252.1 |
| 2015/0168287 A1* | 6/2015 | Kinugasa | ............... | G01N 15/1434 356/51 |
| 2015/0177144 A1* | 6/2015 | Kinugasa | ............... | G01N 15/1434 250/459.1 |
| 2015/0211080 A1* | 7/2015 | Yamasaki | ............... | G01N 15/1459 435/3 |
| 2015/0233704 A1* | 8/2015 | Martini | ............... | G01B 11/046 356/635 |
| 2015/0377785 A1* | 12/2015 | Hosoi | ............... | C12Q 1/06 435/34 |
| 2015/0377786 A1* | 12/2015 | Hosoi | ............... | G01J 1/42 250/216 |
| 2016/0223492 A1* | 8/2016 | Glossop | ............... | G01N 15/12 |
| 2017/0059470 A1* | 3/2017 | Hasegawa | ............... | G01N 21/6458 |
| 2017/0074795 A1* | 3/2017 | Irie | ............... | G01N 21/0332 |

FOREIGN PATENT DOCUMENTS

| | | |
|---|---|---|
| JP | 2000-241335 | 9/2000 |
| JP | 4284031 | 3/2009 |
| JP | 2011-83214 | 4/2011 |
| JP | 4756948 | 6/2011 |
| JP | 2013-117466 | 6/2013 |
| JP | 2013-144057 | 7/2013 |
| JP | 2013-148391 | 8/2013 |

\* cited by examiner

PARTICLE DETECTION APPARATUS AND PARTICLE DETECTION METHOD

CROSS-REFERENCE TO RELATED APPLICATIONS

This application claims priority to Japanese Application No. 2015-088349, filed Apr. 23, 2015, the entire contents of which are incorporated herein by reference.

BACKGROUND OF THE INVENTION

1. Field of the Invention

The present invention relates to a detection technology, and particularly relates to a particle detection apparatus and a particle detection method.

2. Description of the Related Art

In a clean room such as a biological clean room, airborne microbial particles and non-microbial particles are detected and recorded by using a particle detection apparatus (for example, see Japanese Unexamined Patent Application Publication Nos. 2011-83214, 2013-117466, 2013-144057, 2013-148391, and 2000-241335, Japanese Examined Patent Application Publication No. 6-52232, Japanese Patent Nos. 3049254, 4284031, and 4756948, and Norio HASEGAWA et al., "Instantaneous Bioaerosol Detection Technology and Its Application," Yamatake Corporation, azbil Technical Review, December 2009 issue, p. 2-7, 2009). With the detection result for the particles, the degree of deterioration of an air-conditioning apparatus in the clean room can be recognized. Also, the detection record for the particles in the clean room may be attached as a reference material to a product manufactured in the clean room.

An optical particle detection apparatus, for example, sucks gas in the clean room, and irradiates the sucked gas with light. If microbial particles and non-microbial particles are contained in the gas, the particles irradiated with the light emit fluorescence, and scattered light may be generated at the particles. Hence, by detecting the fluorescence and the scattered light, the numbers and sizes of the microbial particles and the non-microbial particles contained in the gas can be detected. Also, a technology of correctly detecting particles in a fluid is desired in an environment other than the clean room (for example, see Japanese Unexamined Patent Application Publication No. 8-29331).

The intensity of fluorescence emitted by particles may vary depending on the kind of the particles. Also, the intensity of scattered light generated at particles may vary depending on the kind of the particles. Hence, there is suggested a method of determining whether the particles are biological particles or non-biological particles on the basis of the intensity of the fluorescence and the intensity of the scattered light.

SUMMARY OF THE INVENTION

An object of the invention is to provide a particle detection apparatus and a particle detection method that can correctly specify the attribute of a particle.

An aspect of the invention provides a particle detection apparatus including (a) an inspection light source that emits inspection light; (b) a plurality of photodetectors that detect reaction light generated at a particle irradiated with the inspection light and generate electric signals in respective channels; (c) a pulse detector that detects pulses of the electric signals in the respective channels; (d) a correlating unit that correlates the pulse of the electric signal in a reference channel being a channel having a highest signal-to-noise ratio, with the pulse of the electric signal in a channel other than the reference channel generated within a predetermined time difference range with respect to the pulse of the electric signal in the reference channel; and (e) an attribute specifying unit that specifies an attribute of the particle on the basis of the correlated pulses of the electric signals.

In the above-described particle detection apparatus, the pulse detector may specify times at which the centers of gravity of the pulses of the electric signals are given, as times at which the pulses appear; and the correlating unit may correlate the pulse of the electric signal in the reference channel with the pulse of the electric signal in a channel other than the reference channel appearing at the time within the predetermined time difference range with respect to the time at which the pulse of the electric signal in the reference channel appears. The pulses of the electric signals may be detected on the basis of intensities of the electric signals.

The reaction light may include scattered light generated at the particle. At least one of the plurality of photodetectors may detect the scattered light. The reaction light may include fluorescence generated at the particle. At least one of the plurality of photodetectors may detect the fluorescence.

Also, another aspect of the invention provides a particle detection method including (a) detecting reaction light generated at a particle irradiated with inspection light by a plurality of photodetectors and generating electric signals in respective channels; (b) detecting pulses of the electric signals in the respective channels; (c) correlating the pulse of the electric signal in a reference channel being a channel having a highest signal-to-noise ratio, with the pulse of the electric signal in a channel other than the reference channel generated within a predetermined time difference range with respect to the pulse of the electric signal in the reference channel; and (d) specifying an attribute of the particle on the basis of the correlated pulses of the electric signals.

In the above-described particle detection method, in the detection of the pulses, times at which the centers of gravity of the pulses of the electric signals are given may be specified as times at which the pulses appear, and the pulse of the electric signal in the reference channel may be correlated with the pulse of the electric signal in a channel other than the reference channel appearing at the time within the predetermined time difference range with respect to the time at which the pulse of the electric signal in the reference channel appears. The pulses of the electric signals may be detected on the basis of intensities of the electric signals.

In the above-described particle detection method, the reaction light may include scattered light generated at the particle. At least one of the plurality of photodetectors may detect the scattered light. The reaction light may include fluorescence generated at the particle. At least one of the plurality of photodetectors may detect the fluorescence.

With the invention, the particle detection apparatus and the particle detection method that can correctly specify the attribute of the particle can be provided.

DESCRIPTION OF THE PREFERRED EMBODIMENTS

An embodiment of the invention is described below. In the description on the drawings, the same or similar reference sign is applied to the same or similar part. The drawings are schematic. Hence, specific dimensions etc. should be judged with reference to the following description. Also, the drawings may include portions with different dimensional relationships and different dimensional ratios as a matter of course.

Figure 1:
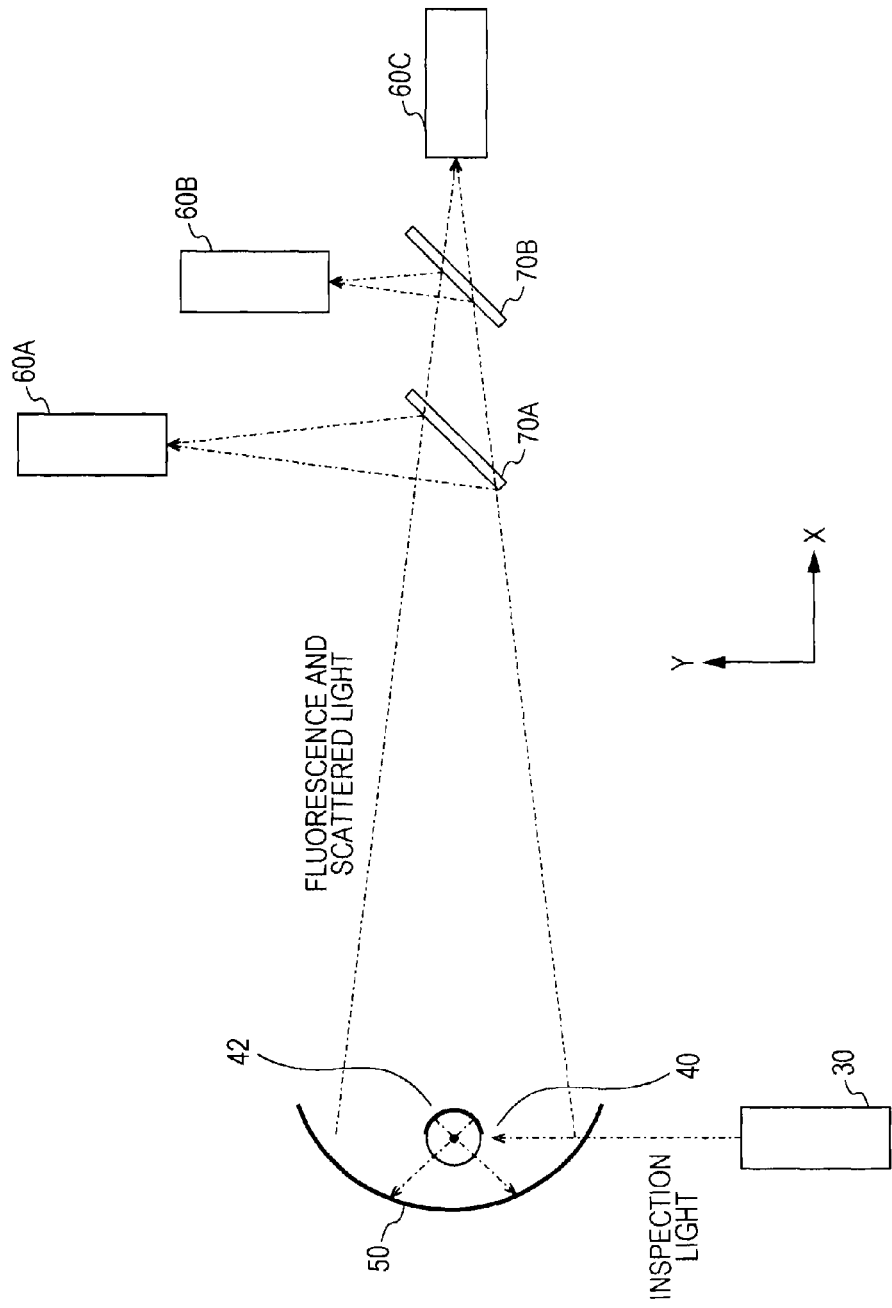
FIG. 1 is a schematic illustration of a particle detection apparatus according to an embodiment of the invention.
Figure 2:
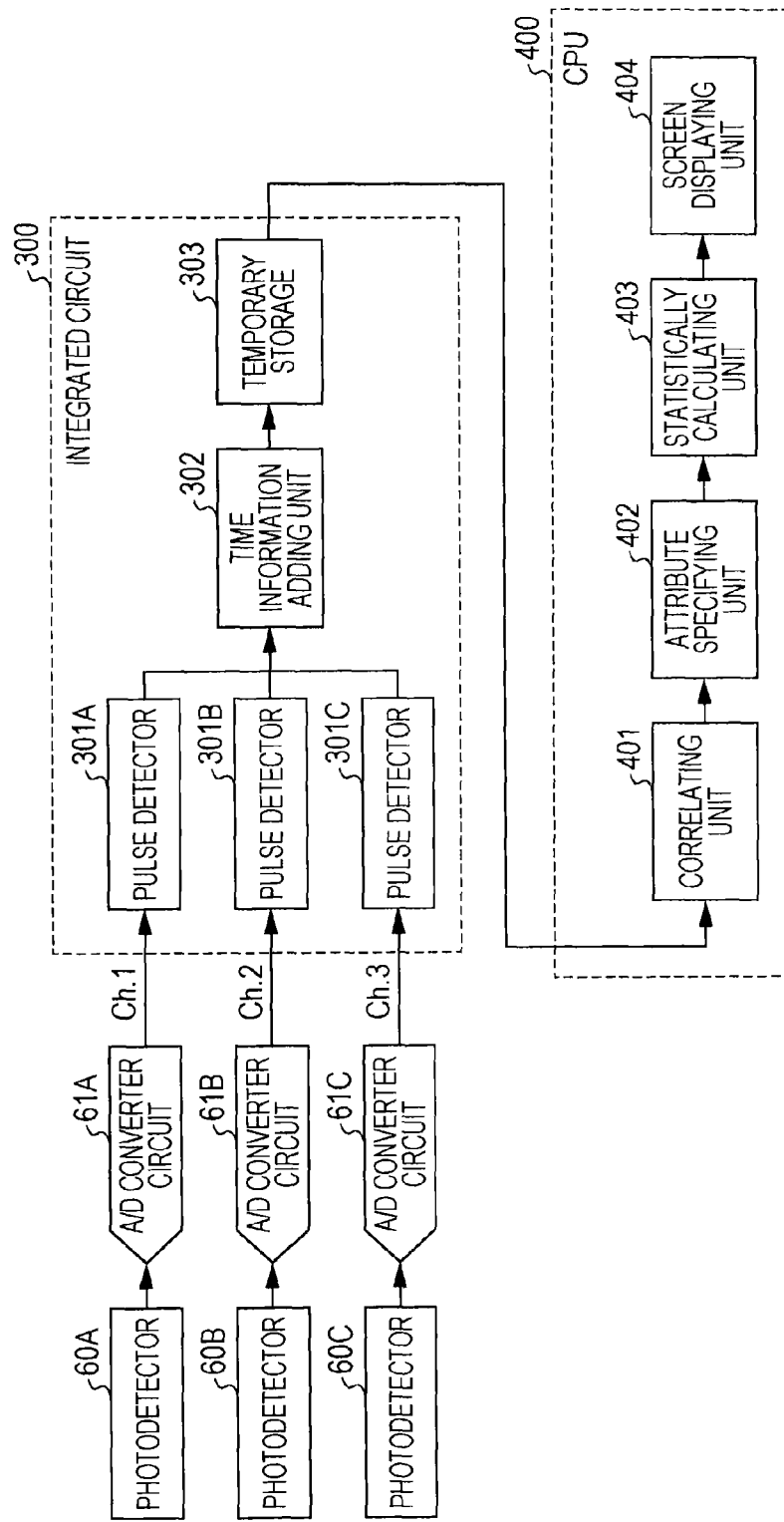
FIG. 2 is a schematic illustration of the particle detection apparatus according to the embodiment of the invention.

As shown in FIGS. 1 and 2, a particle detection apparatus according to the embodiment of the invention includes an inspection light source 30 that emits inspection light; a plurality of photodetectors 60A, 60B, and 60C that detect reaction light generated at a particle irradiated with the inspection light and generate electric signals in respective channels; pulse detectors 301A, 301B, and 301C that detect pulses of the electric signals in the respective channels; a correlating unit 401 that correlates the pulse of the electric signal in a reference channel Ch.1 being a channel having the highest signal-to-noise (S/N) ratio, with the pulses of the electric signals in channels Ch.2 and Ch.3 other than the reference channel Ch.1 generated in a predetermined time difference range with respect to the pulse of the electric signal in the reference channel Ch.1; and an attribute specifying unit 402 that specifies the attribute of the particle on the basis of the correlated pulses of the electric signals.

Particles are contained in, for example, a fluid. In this case, the fluid is, for example, gas or liquid. The fluid containing the particles flows in a transparent flow cell 40 shown in FIG. 1. The flow cell 40 is made of, for example, quartz glass etc. The flow cell 40 is provided with, for example, a reflecting film 42 that reflects the reaction light generated at the particles irradiated with the inspection light. The reflecting film 42 is, for example, an evaporated film, and is made of metal etc. The particle detection apparatus according to the embodiment further includes an elliptic mirror 50 having a first focal point at the position of the flow cell 40. The elliptic mirror 50 reflects the reaction light. The photodetectors 60A, 60B, and 60C are arranged at a second focal point of the elliptic mirror 50, and detect the reaction light reflected by the elliptic mirror 50. In this case, the reaction light is at least one of fluorescence and scattered light.

The particles contained in the fluid flowing in the flow cell 40 include a biological substance including microbes (micro-organisms) etc.; cells; a chemical substance; and dust, such as waste, dirt, and lint. The microbes (micro-organisms) include, for example, bacteria and fungi. Examples of the bacteria are Gram-negative bacteria and Gram-positive bacteria. An example of the Gram-negative bacteria is *Escherichia coli*. Examples of the Gram-positive bacteria are *Staphylococcus epidermidis, Bacillus subtilis, Micrococcus*, and *Corynebaccterium*. An example of the fungi is *Aspergillus* such as black mold. However, the microbes (micro-organisms) are not limited to the above-listed examples.

If fluorescent particles such as microbes (micro-organisms) are contained in the fluid, the particles emit fluorescence when irradiated with excitation light. For example, riboflavin, flavin mononucleotide (FMN), flavin adenine dinucleotide (FAD), nicotinamide adenine dinucleotide phosphoric acid (NAD(P)H), pyridoxamine, pyridoxal-5'-phosphate, pyridoxine, tryptophan, tyrosine, phenylalanine, etc., emit fluorescence. Also, even if the particles are non-biological particles, as long as the particles contain a fluorescent substance, the particles emit fluorescence when irradiated with the excitation light.

The excitation light serving as inspection light for detecting a particle flowing in the flow cell 40 is, for example, emitted from the inspection light source 30 so that the inspection light is focused at the center of the flow cell 40. As the inspection light source 30, a light-emitting diode (LED) or a laser may be used. The inspection light has, for example, a wavelength in a range from 250 nm to 550 nm (inclusive). The inspection light may be visible light or ultraviolet light. If the inspection light is visible light, the inspection light has, for example, a wavelength in a range from 400 nm to 550 nm (inclusive), and is, for example, 405 nm. If the inspection light is ultraviolet light, the inspection light has, for example, a wavelength in a range from 300 nm to 380 nm (inclusive), and is, for example, 340 nm. However, the wavelength of the inspection light is not limited thereto. Also, the inspection light may be white light or mixed light.

A fluorescent particle irradiated with the excitation light in the flow cell 40 emits fluorescence. Also, scattered light caused by Mie scattering is generated at a fluorescent particle and a non-fluorescent particle irradiated with the excitation light. The fluorescence and scattered light as reaction light generated at the particles irradiated with the light reach the elliptic mirror 50. The fluorescence and scattered light emitted from the surface of the flow cell 40 are reflected by the elliptic mirror 50, and are condensed at the second focal point of the elliptic mirror 50 located behind the flow cell 40. Wavelength-selective reflecting mirrors 70A and 70B are arranged between the geometrical first focal point and second focal point of the elliptic mirror 50.

For example, the wavelength-selective reflecting mirror 70A reflects scattered light wavelength-selectively. The focal point of the scattered light reflected by the wavelength-selective reflecting mirror 70A is optically equivalent to the geometrical second focal point of the elliptic mirror 50. The photodetector 60A for detecting the scattered light is arranged at the focal point of the scattered light reflected by the wavelength-selective reflecting mirror 70A. A band pass filter including a dielectric multilayer film or the like, a long pass filter, etc., may be arranged between the wavelength-selective reflecting mirror 70A and the photodetector 60A.

The wavelength-selective reflecting mirror 70B, for example, reflects fluorescence in a first wavelength band and transmits fluorescence in a second wavelength band wavelength-selectively. The focal point of the fluorescence reflected by the wavelength-selective reflecting mirror 70B is optically equivalent to the geometrical second focal point of the elliptic mirror 50. The photodetector 60B for detecting the fluorescence in the first wavelength band is arranged at the focal point of the fluorescence in the first wavelength band reflected by the wavelength-selective reflecting mirror 70B. The photodetector 60C for detecting the fluorescence in the second wavelength band different from the first wavelength band is arranged at the focal point of the fluorescence in the second wavelength band transmitted through the wavelength-selective reflecting mirror 70B. A band pass filter including a dielectric multilayer film or the like, a long pass filter, etc., may be arranged between the wavelength-selective reflecting mirror 70B and the photodetector 60B, and between the wavelength-selective reflecting mirror 70B and the photodetector 60C.

As the wavelength-selective reflecting mirrors 70A and 70B, dichroic mirrors, interference film filters, optical filters, etc., may be used.

The photodetectors 60A, 60B, and 60C photoelectrically convert received reaction light and generate electric signals. As the photodetectors 60A, 60B, and 60C, photodiodes, photomultiplier tubes (PMT), etc. may be used. The photodetectors 60A, 60B, and 60C may be the same model or different models.

As shown in FIG. 2, the photodetectors 60A, 60B, and 60C are respectively connected to analog-to-digital (A/D) converter circuits 61A, 61B, and 61C. The A/D converter circuits 61A, 61B, and 61C convert analog electric signals into digital electric signals. The A/D converter circuits 61A, 61B, and 61C may include low pass filters that eliminate high-frequency noise. In this case, for example, it is assumed that an electric signal derived from the photodetector 60A has the highest S/N ratio.

Figure 3:
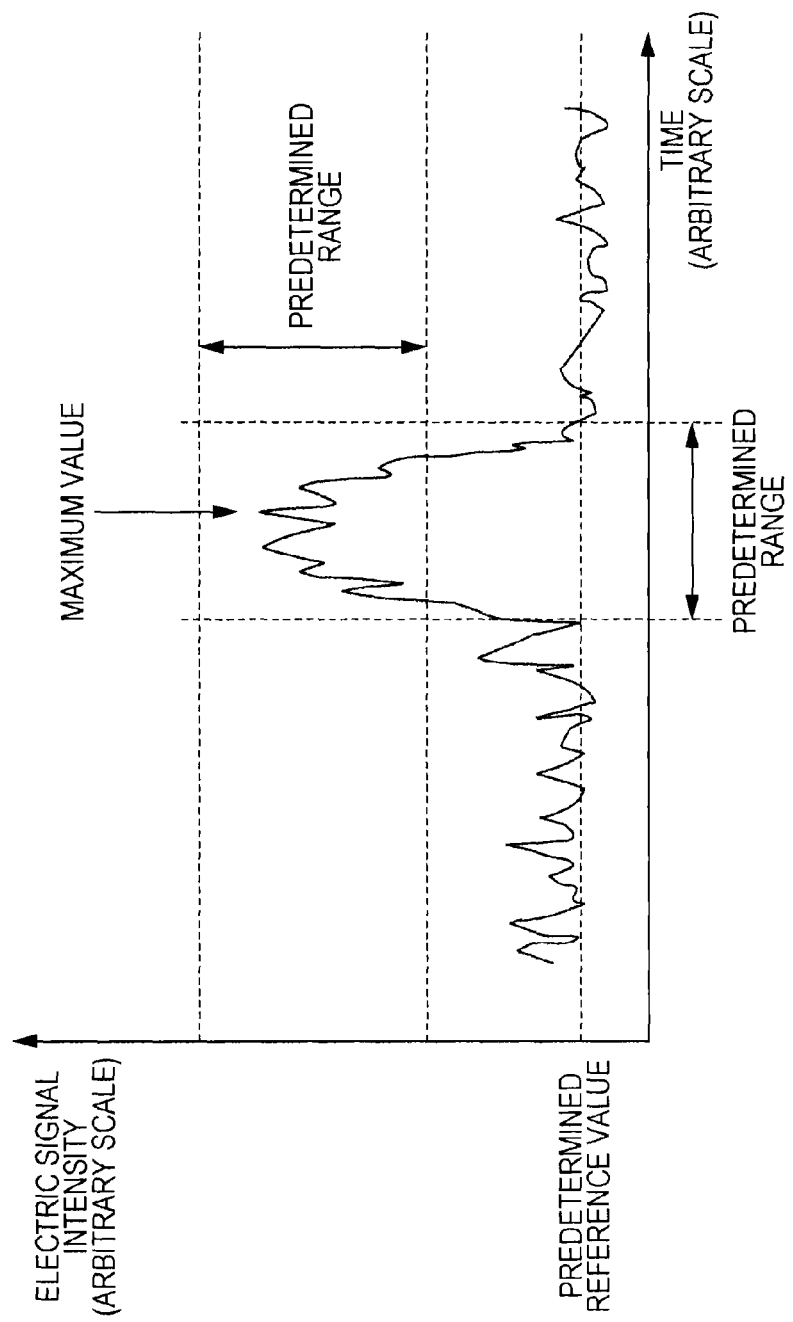
FIG. 3 is a schematic illustration showing a pulse of an electric signal according to the embodiment of the invention.

The pulse detector 301A detects an electric signal pulse waveform corresponding to a light intensity waveform of reaction light detected by the photodetector 60A. For example, as shown in FIG. 3, the pulse detector 301A detects, as a pulse, a partial waveform, in which a period after the voltage intensity of the electric signal exceeds a predetermined reference value until the voltage intensity falls short of the predetermined reference value is within a predetermined range along the time axis, and in which the maximum value of the voltage intensity of the electric signal is within a predetermined range.

Figure 4:
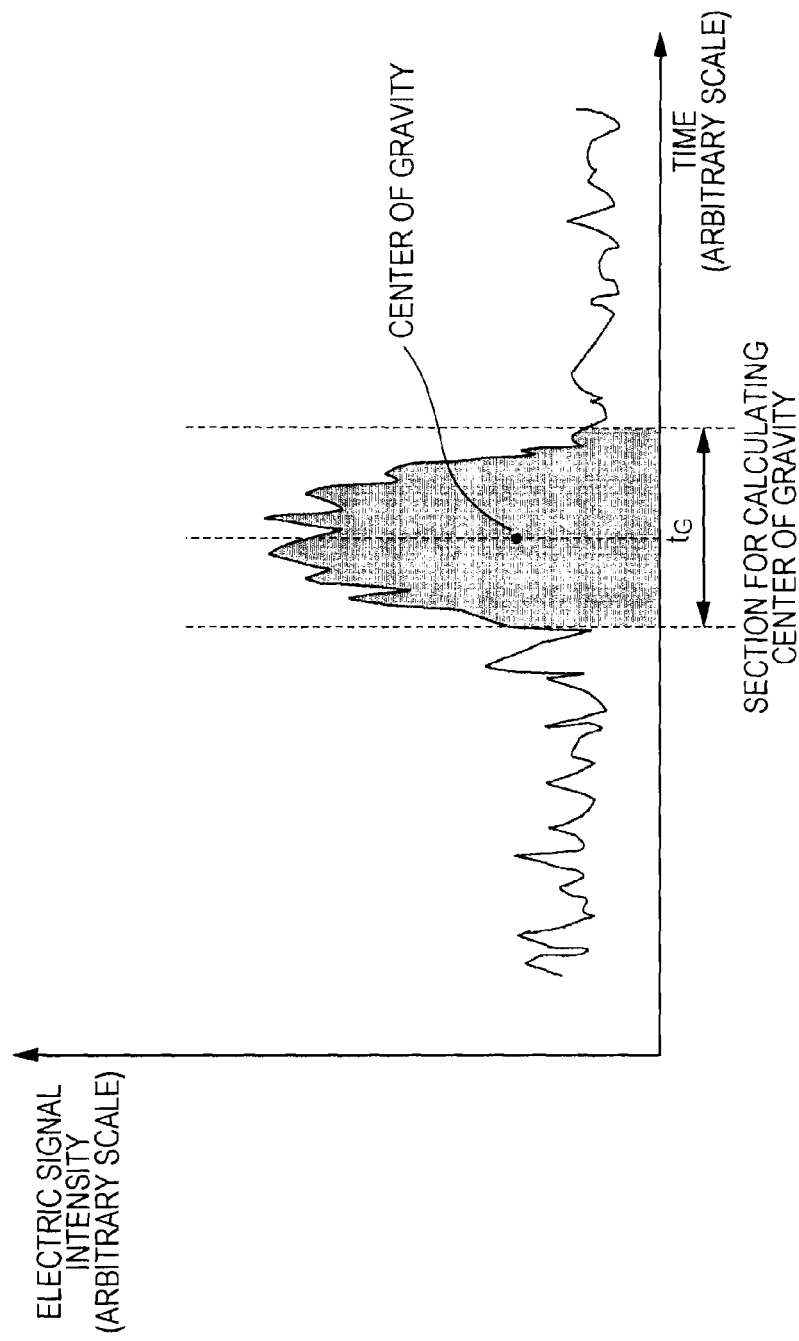
FIG. 4 is a schematic illustration showing a pulse of an electric signal according to the embodiment of the invention.
Figure 5:
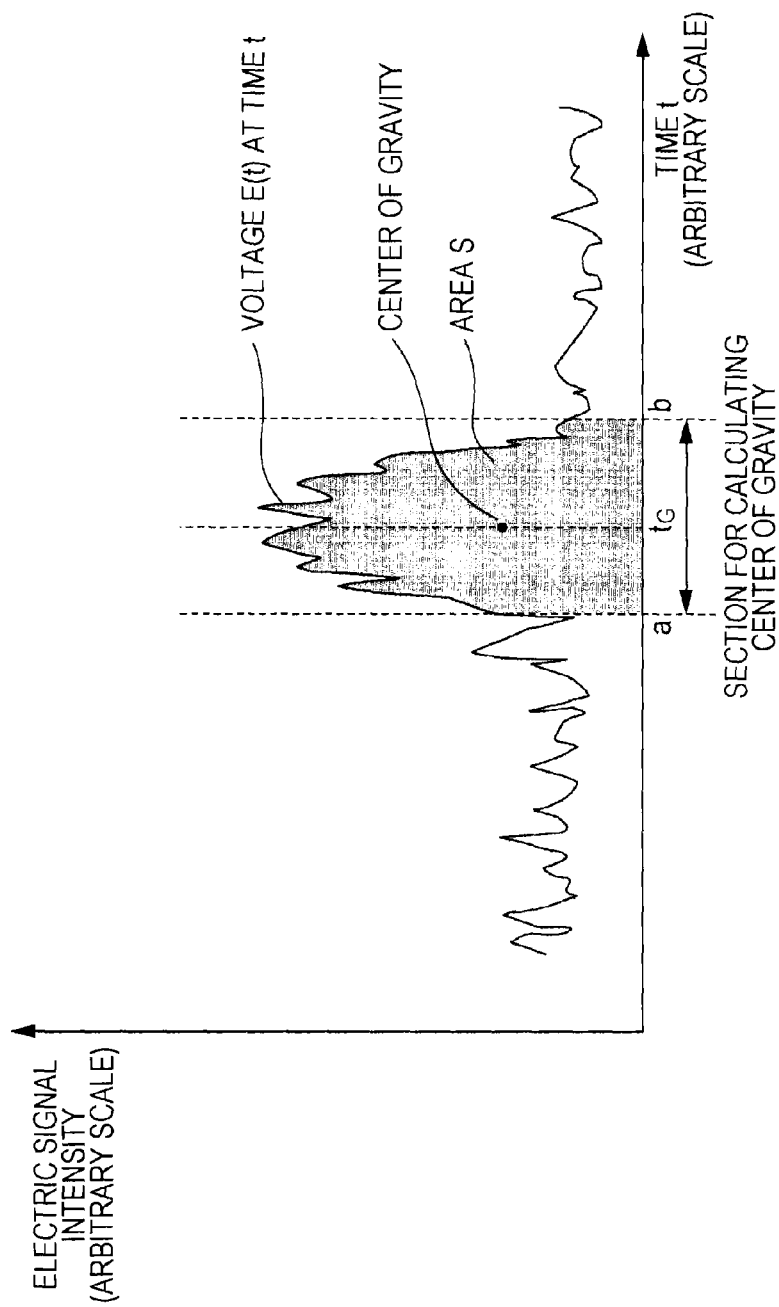
FIG. 5 is a schematic illustration showing a pulse of an electric signal according to the embodiment of the invention.

As shown in FIG. 4, the pulse detector 301A may further calculate a time of the center of gravity of the detected pulse along the time axis, as the time at which the pulse appears. For example, when S represents an area given by integrating the pulse waveform, a time $t_G$ of the center of gravity along the time axis t in a portion surrounded by the pulse waveform can be calculated by Expression (1) as follows. If the pulse waveform is treated as discrete data, as shown in FIG. 5, when E(t) represents a voltage at a time t and a section in a period t for calculating the center of gravity is between a and b (inclusive), a time $t_G$ of the center of gravity in a portion surrounded by the pulse waveform along the time axis t can be calculated by Expression (2) as follows. However, the method of calculating the time at which the pulse appears is not limited thereto. For example, a time at which the maximum value of movement average of the electric signal pulse waveform may be calculated as the time at which the pulse appears.

$$t_G = (1/S) \int t ds \quad (1)$$

$$t_G = \frac{1}{S} \sum_{t=a}^{b} E(t)t \quad (2)$$

The pulse detector 301A shown in FIG. 2 outputs pulse information including the channel, peak height, and width of the detected pulse, the time at which the pulse appears, a range-over flag, etc. The peak height may be the maximum intensity of the pulse, or the intensity of the pulse at the center of gravity.

The pulse detector 301B detects an electric signal pulse waveform corresponding to a light intensity waveform of reaction light detected by the photodetector 60B, and outputs pulse information. The pulse detector 301C detects an electric signal pulse waveform corresponding to a light intensity waveform of reaction light detected by the photodetector 60C, and outputs pulse information. The method of detecting the pulses and outputting the pulse information by the pulse detectors 301B and 301C is similar to that of the pulse detector 301A.

The particle detection apparatus according to the embodiment may further include a time information adding unit 302. The time information adding unit 302 calculates a relative time for the time at which the detected pulse appears, relative to the time at which a pulse stored in a temporary storage 303 (described later) appears immediately before the pulse is detected. The time information adding unit 302 adds the calculated relative time to the pulse information.

The pulse information is stored in the temporary storage 303. As the temporary storage 303, a first-in first-out (FIFO) buffer etc. may be used. By employing the FIFO buffer, even if acquisition of data on pulse information by a central processing unit 400 (described later) is temporarily delayed, the data can be prevented from being missed. Further, the pulse information may be stored in a long-term storage such as a hard disk.

The processing executed by the pulse detectors 301A and 301B and the time information adding unit 302 tends to require high speed and real time capabilities. The required amount of calculation also tends to increase. Also, the pulse information typically has a small data size. Hence, the pulse detectors 301A and 301B, the time information adding unit 302, and the temporary storage 303 are preferably realized by an integrated circuit 300 such as a field programmable gate array (FPGA). However, it is not limited thereto.

The correlating unit 401 correlates the pulse of the electric signal derived from the photodetector 60A and having the highest S/N ratio with a pulse of an electric signal derived from another photodetector appearing at a relative time within a predetermined time difference range with respect to the time at which the electric signal derived from the photodetector 60A and having the highest S/N ratio appears. In this case, the predetermined time difference is previously set on the basis of, for example, a difference in delay time of each of the channels Ch.1, Ch.2, and Ch.3. Alternatively, for example, the correlating unit 401 may correlate pulses generated in a predetermined time difference range and having peak heights in a predetermined range with each other.

For example, if the relative time at which the pulse of the electric signal derived from the photodetector 60B appears is within the predetermined time difference range with respect to the time at which the pulse of the electric signal derived from the photodetector 60A appears, the correlating unit 401 correlates the pulse of the electric signal derived from the photodetector 60A with the pulse of the electric signal derived from the photodetector 60B. If the relative time at which the pulse of the electric signal derived from the photodetector 60B appears is not within the predetermined time difference range with respect to the time at which the pulse of the electric signal derived from the photodetector 60A appears, the correlating unit 401 does not correlate the pulse of the electric signal derived from the photodetector 60A with the pulse of the electric signal derived from the photodetector 60B.

If a plurality of pulses of the electric signal derived from the photodetector 60B appear within the predetermined time difference range for the pulse of the electric signal derived from the photodetector 60A, the correlating unit 401 may correlate the pulse at the earliest relative time of the electric signal derived from the photodetector 60B with the pulse of the electric signal derived from the photodetector 60A. Alternatively, the correlating unit 401 may correlate the pulse with the largest peak height among the plurality of pulses of the electric signal derived from the photodetector 60B appearing within the predetermined time difference range, with the pulse of the electric signal derived from the photodetector 60A. Accordingly, one pulse of the electric signal derived from the photodetector 60B can be correlated with one pulse of the electric signal derived from the photodetector 60A.

In the case in which the plurality of pulses of the electric signal derived from the photodetector 60B appear within the predetermined time difference range, a user of the particle detection apparatus may determine which one of the pulse at the earliest relative time and the pulse with the largest peak height of the electric signal derived from the photodetector 60B is correlated with the pulse of the electric signal derived from the photodetector 60A, depending on the particle to be detected.

Also, for example, if the relative time at which the pulse of the electric signal derived from the photodetector 60C appears is within the predetermined time difference range with respect to the time at which the pulse of the electric signal derived from the photodetector 60A appears, the correlating unit 401 correlates the pulse of the electric signal derived from the photodetector 60A with the pulse of the electric signal derived from the photodetector 60C. If the relative time at which the pulse of the electric signal derived from the photodetector 60C appears is not within the predetermined time difference range with respect to the time at which the pulse of the electric signal derived from the photodetector 60A appears, the correlating unit 401 does not correlate the pulse of the electric signal derived from the photodetector 60A with the pulse of the electric signal derived from the photodetector 60C.

If a plurality of pulses of the electric signal derived from the photodetector 60C appear within the predetermined time difference range for the pulse of the electric signal derived from the photodetector 60A, the correlating unit 401 may correlate a pulse at the earliest relative time of the electric signal derived from the photodetector 60C with the pulse of the electric signal derived from the photodetector 60A. Alternatively, the correlating unit 401 may correlate a pulse with the largest peak height among the plurality of pulses of the electric signal derived from the plurality of photodetectors 60C appearing within the predetermined time difference range, with the pulse of the electric signal derived from the photodetector 60A. Accordingly, one pulse of the electric signal derived from the photodetector 60C can be correlated with one pulse of the electric signal derived from the photodetector 60A.

In the case in which the plurality of pulses of the electric signal derived from the photodetector 60C appear within the predetermined time difference range, the user of the particle detection apparatus may determine which one of the pulse at the earliest relative time and the pulse with the largest peak height of the electric signal derived from the photodetector 60C is correlated with the pulse of the electric signal derived from the photodetector 60A, depending on the particle to be detected.

The correlated pulses are derived from reaction light generated at the same particle. Also, information indicative of a single pulse is added to a particle not correlated with any of pulses. For example, if the pulse of the electric signal derived from the photodetector 60B or 60C that detects fluorescence in the first or second wavelength band is not correlated with the pulse of the electric signal derived from the photodetector 60A that detects scattered light, it may be expected that the particle is a non-fluorescent particle and only scattered light is generated from the particle. If the pulse of the electric signal derived from the photodetector 60B is correlated with the pulse of the electric signal derived from the photodetector 60A, it may be expected that the particle is a fluorescent particle and scattered light and fluorescence in the first wavelength band are generated from the particle. If the pulses of the electric signals derived from the photodetectors 60B or 60C are correlated with the pulse of the electric signal derived from the photodetector 60A, it may be expected that the particle is a fluorescent particle and scattered light and fluorescence in the first and second wavelength bands are generated from the particle.

The attribute specifying unit 402 specifies the attribute of the particle from the pulse information on the correlated pulses. The attribute of the particle includes the kind, material, and size of the particle. For example, the intensity of the scattered light tends to be correlated with the particle diameter of the particle. Also, the wavelength and intensity of the fluorescence emitted by a microbial particle tend to be correlated with the kind of the microbial particle. Further, the wavelength and intensity of the fluorescence emitted by a non-biological fluorescent particle tend to be correlated with the kind and material of the non-biological fluorescence particle. The ratio of fluorescence intensities with different wavelengths emitted by the microbial particle or the non-biological fluorescent particle tends to be correlated with the kind and material of the particle. Further, if the non-biological particle is formed of a material not containing a fluorescent substance, the non-biological particle does not emit fluorescence. Accordingly, the attribute of the particle can be specified from the pulse information. The attribute specifying unit 402 specifies the attribute of a particle also from pulse information on a single pulse. For example, if a particle is a non-biological particle not containing a fluorescent substance, only a pulse derived from scattered light is generated. Hence the attribute specifying unit 402 specifies the attribute of the particle on the basis of only the pulse derived from the scattered light. The attribute specifying unit 402 may specify the attribute of a particle generating a pulse by using an estimation function such as a support vector machine (SVM) while using the pulse information as an argument.

The particle detection apparatus according to the embodiment may further include a statistically calculating unit 403 and a screen displaying unit 404. The statistically calculating unit 403 calculates a statistic value relating to a particle whose attribute has been specified. For example, the statistically calculating unit 403 calculates the number per fluid volume of particles whose attribute has been specified, the total number of particles which have been detected within a predetermined period and whose attribute has been specified, histogram, and time-lapse change. The screen displaying unit 404 instructs a display device to display the operating state of the particle detection apparatus, the attribute of the particle specified by the attribute specifying unit 402, and the statistic value relating to the particle calculated by the statistically calculating unit 403.

The frequency of generation of data to be processed by the correlating unit 401, the attribute specifying unit 402, the statistically calculating unit 403, and the screen displaying unit 404 tends to be lower than the frequency of generation of data to be processed by the pulse detectors 301A and 301B and the time information adding unit 302. Also, the data to be processed by the correlating unit 401, the attribute specifying unit 402, the statistically calculating unit 403, and the screen displaying unit 404 tends to be more easily treated with order processing than the data to be processed by the pulse detectors 301A and 301B and the time information adding unit 302. Hence, for example, the correlating unit 401, the attribute specifying unit 402, the statistically calculating unit 403, and the screen displaying unit 404 are preferably realized by the central processing unit (CPU); however, it is not limited thereto.

In the particle detection apparatus according to the embodiment, by assigning data processing to the FPGA and CPU in accordance with the content of the data processing, the manufacturing cost, power consumption, and size of the particle detection apparatus can be decreased.

Figure 6:
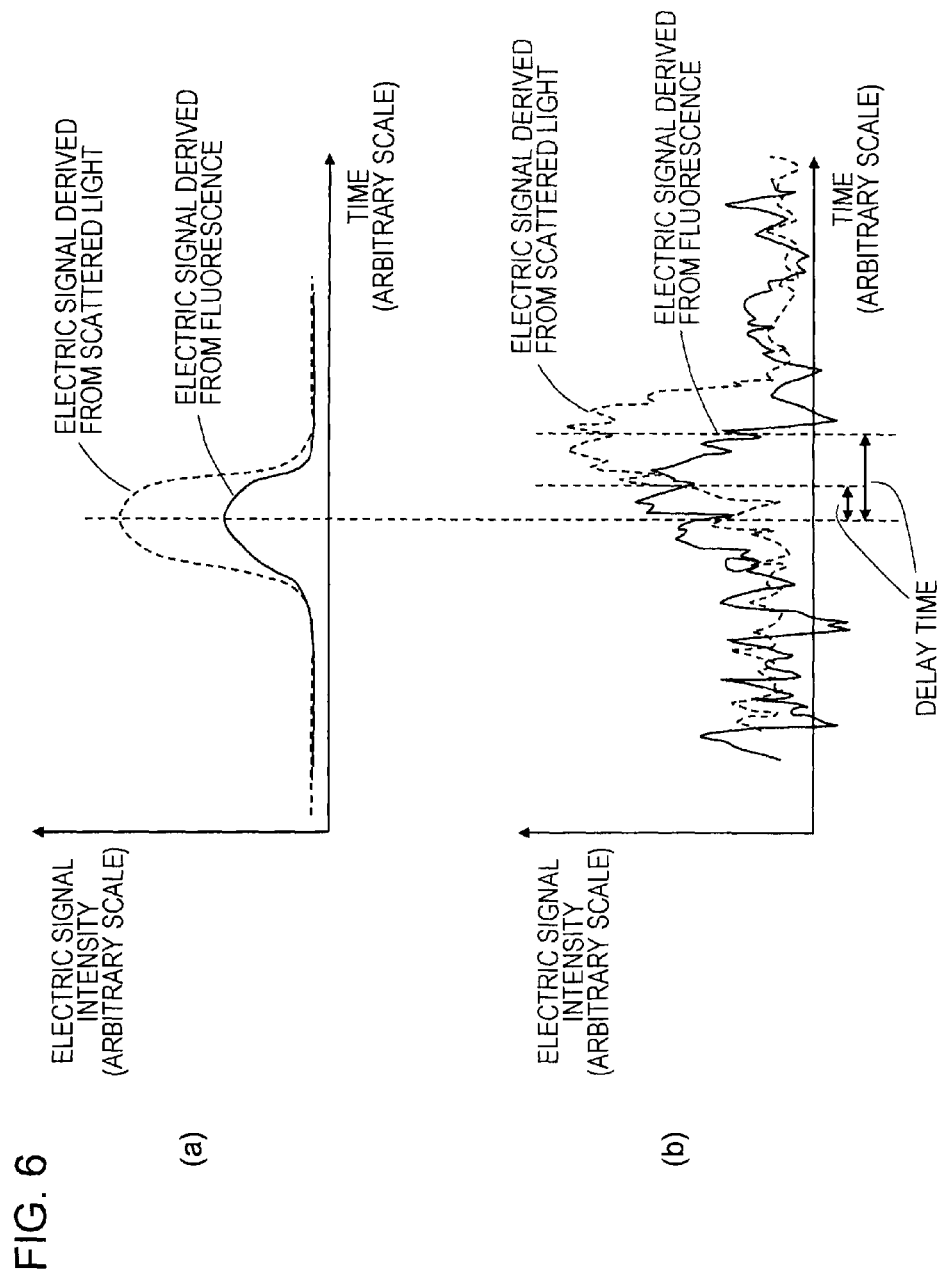
FIG. 6 is a schematic illustration showing pulses of electric signals according to the embodiment of the invention.

For example, when scattered light and fluorescence in the first wavelength band are generated at a particle irradiated with inspection light, the electric signal derived from the photodetector 60A that detects the scattered light and the electric signal derived from the photodetector 60B that detects the fluorescence in the first wavelength band ideally have pulses appearing at the same time and the pulses preferably have the same width and center as shown in part (a) in FIG. 6. However, the electric signals actually have noise as shown in part (b) in FIG. 6. Also, due to the difference in response speed between the photodetectors and in group delay characteristics of amplifiers connected to the photodetectors, the pulse of the electric signal derived from the photodetector 60A that detects the scattered light and the pulse of the electric signal derived from the photodetector 60B that detects the fluorescence in the first wavelength band do not always appear at the same time. The same phenomenon occurs in the pulse of the electric signal derived from the photodetector 60C. Owing to this, if it is expected that the pulse that does not appear at the same time is derived from reaction light generated from another particle, a single particle may be incorrectly detected as a plurality of particles.

In contrast, the particle detection apparatus according to the embodiment correlates the pulse of the electric signal in the reference channel having the highest S/N ratio whose pulse is easily detected, with the pulse of the electric signal in a channel other than the reference channel generated within the predetermined time difference range with respect to the pulse of the electric signal in the reference channel; and specifies the attribute of the single particle on the basis of the correlated pulses of the electric signals. Accordingly, a single particle can be prevented from being incorrectly detected as a plurality of particles. Further, instead of retrieving a pulse generated by a time difference without a range with respect to the pulse of the electric signal in the reference channel, by retrieving the pulse generated within the predetermined time difference range, the influence of the incorrect detection at the time at which the pulse appears can be restricted. Furthermore, even if the pulse waveforms generated in the respective channels are not superimposed, the pulse of the electric signal in the reference channel can be correlated with a pulse of an electric signal in a channel other than the reference channel generated within the predetermined time difference range with respect to the pulse of the electric signal in the reference channel.

Also, the speed at which the particle passes through the flow cell may vary depending on a portion in the flow cell. To be specific, the flow rate of fluid is the highest at a position near the center of the flow cell, and the flow rate of fluid tends to be lowered toward the side wall of the flow cell. Hence, even with the same kind of particles, the width of a pulse derived from reaction light emitted by a particle flowing at a position near the center of the flow cell tends to decrease, and the width of a pulse derived from reaction light emitted by a particle flowing at a position near the side wall of the flow cell tends to increase. Further, the flow rate of fluid flowing in the flow cell may entirely vary. Furthermore, the speed of a particle flowing in the flow cell may vary depending on the particle diameter of the particle, and the intensity of reaction light generated by a particle may vary depending on the kind of the particle.

In contrast, the particle detection apparatus according to the embodiment calculates the time at which the pulse appears by calculating the center of gravity of the pulse waveform. To calculate the center of gravity, a pulse waveform in a constant period is used. Hence, the influence of noise can be restricted. Also, the influence of change in width or height of a pulse on detection of the pulse position can be restricted.

OTHER EMBODIMENTS

The embodiment of the invention has been described above; however, it should not be understood that the description and drawings constituting part of this disclosure limit the invention. With this disclosure, various alternative embodiments, examples, and operating technologies may be apparent to those skilled in the art. For example, FIG. 1 shows the example in which the reaction light generated at the particle is detected by the photodetectors 60A, 60B, and 60C through the elliptic mirror 50. Alternatively, the reaction light generated at the particle may be detected by the photodetectors 60A, 60B, and 60C without the elliptic mirror 50. Still alternatively, the reaction light generated by the particle may be detected by the photodetectors 60A, 60B, and 60C through a lens optical system.

Also, FIG. 1 shows the example in which the particle detection apparatus includes the three photodetectors 60A, 60B, and 60C; however, the number of photodetectors included in the particle detection apparatus is not limited thereto, and the number may be desirably determined as long as being plural. Further, in the particle detection apparatus, a plurality of photodetectors may detect only fluorescence or only scattered light. Furthermore, in the embodiment, the channel Ch.1 for the electric signal derived from the photodetector 60A has the highest S/N ratio. However, the channel Ch.2 for the electric signal derived from the photodetector 60B may have the highest S/N ratio, or the channel Ch.3 for the electric signal derived from the photodetector 60C may have the highest S/N ratio.

Alternatively, the photodetectors may be arranged at different angles to the flow cell, and the pulse detector may add the advancement direction of the reaction light to the pulse information, and the attribute specifying unit may specify the attribute of the particle from the pulse information including the advancement direction of the reaction light. In this way, it should be understood that the invention includes various embodiments etc. not described in this specification.

Although not limited to the configurations listed below, the particle detection apparatus according to the invention may be also used as a biological substance detection apparatus, a bacterial detection apparatus, a microbial detection apparatus, a cell detection apparatus, a flow cytometer, etc.

What is claimed is:

1. A particle detection apparatus comprising:
   an inspection light source that emits inspection light;
   a plurality of photodetectors that detect reaction light generated at a particle irradiated with the inspection light and generate electric signals in respective channels;
   a pulse detector that detects pulses of the electric signals in the respective channels;
   a correlating unit that correlates the pulse of the electric signal in a reference channel being a channel having a highest signal-to-noise ratio, with the pulse of the electric signal in a channel other than the reference channel generated within a predetermined time difference range with respect to the pulse of the electric signal in the reference channel; and
   an attribute specifying unit that specifies an attribute of the particle on the basis of the correlated pulses of the electric signals.

2. The particle detection apparatus according to claim 1, wherein the pulse detector specifies times at which the centers of gravity of the pulses of the electric signals are given, as times at which the pulses appear, and
   wherein the correlating unit correlates the pulse of the electric signal in the reference channel with the pulse of the electric signal in a channel other than the reference channel appearing at the time within the predetermined time difference range with respect to the time at which the pulse of the electric signal in the reference channel appears.

3. The particle detection apparatus according to claim 1, wherein the pulses of the electric signals are detected on the basis of intensities of the electric signals.

4. The particle detection apparatus according to claim 1, wherein the reaction light includes scattered light generated at the particle.

5. The particle detection apparatus according to claim 4, wherein at least one of the plurality of photodetectors detects the scattered light.

6. The particle detection apparatus according to claim 1, wherein the reaction light includes fluorescence generated at the particle.

7. The particle detection apparatus according to claim 6, wherein at least one of the plurality of photodetectors detects the fluorescence.

8. A particle detection method comprising:
   detecting reaction light generated at a particle irradiated with inspection light by a plurality of photodetectors and generating electric signals in respective channels;
   detecting pulses of the electric signals in the respective channels;
   correlating the pulse of the electric signal in a reference channel being a channel having a highest signal-to-noise ratio, with the pulse of the electric signal in a channel other than the reference channel generated within a predetermined time difference range with respect to the pulse of the electric signal in the reference channel; and
   specifying an attribute of the particle on the basis of the correlated pulses of the electric signals.

9. The particle detection method according to claim 8,
   wherein, in the detection of the pulses, times at which the centers of gravity of the pulses of the electric signals are given are specified as times at which the pulses appear, and
   wherein the pulse of the electric signal in the reference channel is correlated with the pulse of the electric signal in a channel other than the reference channel appearing at the time within the predetermined time difference range with respect to the time at which the pulse of the electric signal in the reference channel appears.

10. The particle detection method according to claim 8, wherein the pulses of the electric signals are detected on the basis of intensities of the electric signals.

11. The particle detection method according to claim 8, wherein the reaction light includes scattered light generated at the particle.

12. The particle detection method according to claim 11, wherein at least one of the plurality of photodetectors detects the scattered light.

13. The particle detection method according to claim 8, wherein the reaction light includes fluorescence generated at the particle.

14. The particle detection method according to claim 13, wherein at least one of the plurality of photodetectors detects the fluorescence.

* * * * *